United States Patent [19]

Radulović et al.

[11] 4,180,870
[45] Jan. 1, 1980

[54] UNIVERSAL-ORTHESE

[75] Inventors: Radoje Radulović, Ilidza-Sarajewo; Mustafa Karisik, Sarajewo, both of Yugoslavia; Klaus R. Wolfer, Stuttgart, Fed. Rep. of Germany

[73] Assignee: Fa Wilh. Jul. Teufel, Stuttgart, Fed. Rep. of Germany

[21] Appl. No.: 676,879

[22] Filed: Apr. 14, 1976
(Under 37 CFR 1.47)

[30] Foreign Application Priority Data

Apr. 15, 1975 [YU] Yugoslavia ............................ 948/75

[51] Int. Cl.$^2$ ............................................. A61F 1/00
[52] U.S. Cl. .......................................... 3/1.2; 3/12.1; 128/77
[58] Field of Search .................. 3/1.2, 1.1, 12, 12.1, 3/12.6; 128/77

[56] References Cited

U.S. PATENT DOCUMENTS

| 2,535,489 | 12/1950 | Edwards | 3/1.1 X |
| 3,449,769 | 7/1969 | Mizen | 3/1.2 |
| 4,078,670 | 3/1978 | Francois et al. | 3/1.1 X |

FOREIGN PATENT DOCUMENTS

| 498003 | 1/1976 | U.S.S.R. | 3/1.1 |

OTHER PUBLICATIONS

"A Progress Report on a Programmed Orthotic Arm", Bahniuk, Med. Electron Biol. Engng., vol. 1, No. 4, 12/63, pp. 509–517.
"Hendon Pneumatic Power Units & Controls for Prosthesis & Splints", Wilson, Journal of Bone & Joint Surgery, vol. 47B, No. 3, 8/65, pp. 435–441.
"Development of Externally Powered Upper Extremity Orthotic Systems", Engen, Journal of Bone & Joint Surgery, vol. 47B, No. 3, 8/65, pp. 465–468.
"A System of Powered Prosthesis for Severe Bilateral Upper Limb Deficiency", Simpson, Journal of Bone & Joint Surgery, vol. 47B, No. 3, 8/65, pp. 442–447.

Primary Examiner—E. H. Eickholt

[57] ABSTRACT

An orthesis has a lever system having fulcrum simulating the patient's shoulder joint. The system includes a series of levers facing the patient's trunk to which is applied a force corresponding to that which is represented by the weight of the arm. The force is applied on the lever system at a point which is variable in response to the movement of the arm so that it approximately lies on the line between the center of gravity of the arm and the fulcrum joint.

12 Claims, 5 Drawing Figures

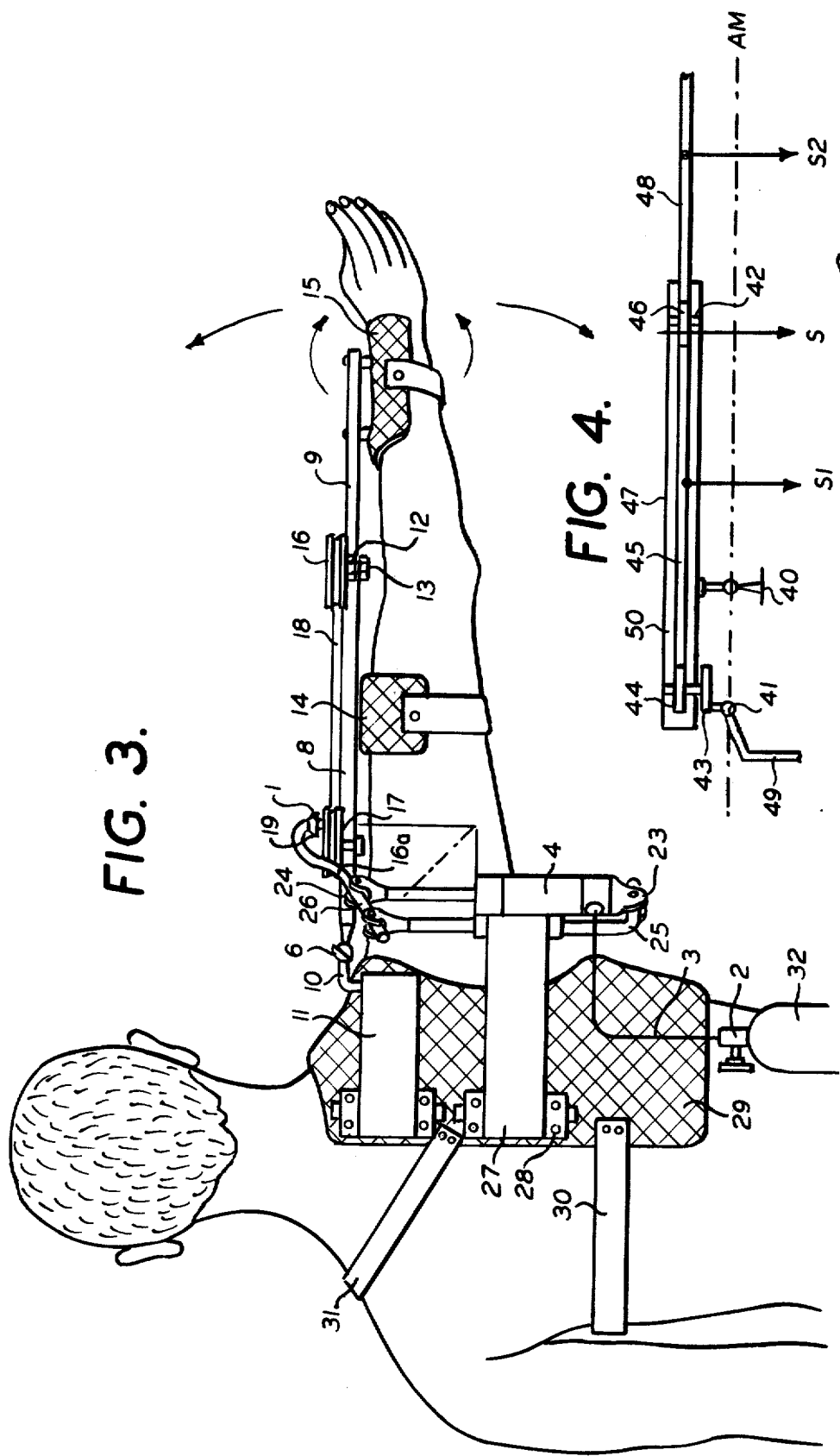

UNIVERSAL-ORTHESE

BACKGROUND OF THE INVENTION

The present invention relates to an orthesis for the upper limbs and in particular to an orthesis having a substantial universal degree of movement. Such an orthesis can be employed successfully if in the region in which it is to be used, i.e. arms, there is still a residue of functional capacity.

The causes of the weakening of normal functioning capacity are many, and may be either supposed or known. A congenital deficiency may be involved, or else as a consequence of disease, accident, or a loss of performance due to advanced age.

In the presence of such debility, all or many functions and movements are possible, although they cannot be performed without support from outside, since the main obstacle to the execution of normal functions and movements of the limbs is the deadweight of the weakened limb.

The object of the present invention is to provide an orthesis which, in the presence of residual functional capacity permits as far as possible all the movements of the weakened limb.

SUMMARY OF THE INVENTION

According to the present invention, an orthesis is provided comprising a lever system having fulcrum simulating the patient's shoulder joint, and a system of levers facing the patient's trunk acted on by a force corresponding to that which is represented by the weight of the arm. The fulcrum after the manner of a universal ball or cardan joint, allows spatial twisting, while the system of levers facing the patient's trunk varies in effective space and length as a function of shifts in the relative position, so that the center of gravity of the arm also varies in every position of the arm. The center of gravity of the arm and the point of application of the force acting on the lever on the trunk side according to the present invention lie on a straight line passing through the fulcrum, which line runs with a high degree of approximation to the shoulder joint.

The invention makes it possible in an advantageous way to perform natural movements of the arm in space.

To enable the orthesis to be worn, a bodice for securement to the upper part of the patient's body is provided.

According to a further embodiment of the invention, provision is made for the lever system to comprise a series of levers following the course of the arm, and preferably consisting of two individual levers articulated to one another; the first of which runs parallel to the upper arm and is connected with the latter and the second one extends parallel to the lower arm and is connected with the latter. A joint, located at the elbow connects the two levers.

It has been found that there is thus obtained on the one hand sufficient simulation of the lever conditions of the natural arm and on the other hand the design cann be carried out very simply.

The invention provides for an eccentric cam system as the means by which the applied force is linked to the upper arm lever, which varies the effective length of the lever system through the rotation of the eccentric cam in response solely to the movement of the individual lever connected with the forearm. This can be accomplished by a belt drive connected to the lever system.

Thus, in an amazingly simple manner, the variation of the position of the center of gravity of the arm is transformed into a variation of the counter-lever formed by or simulated by the eccentric cam.

A design of the universal orthesis, which is pleasant for the patient resides in the fact that the force acting on the lever system is obtained from a reversible energy store attached to the bodice and a connecting bracket so that the entire orthesis forms one constructional unit. A pneumatic force system provides a design whereby low weight is possible.

The invention is further explained below by reference to the accompanying drawings in which:

BRIEF DESCRIPTION OF THE DRAWINGS

FIG. 3 is a rear view of the device shown in FIG. 2,

FIG. 4 is a view taken in the direction of FIG. 2 showing in an analogous diagram a second embodiment of the present invention; and FIG. 5 is a view of the device of FIG. 4 is an analogous view of FIG. 3.

DESCRIPTION OF THE INVENTION

Figure 1:
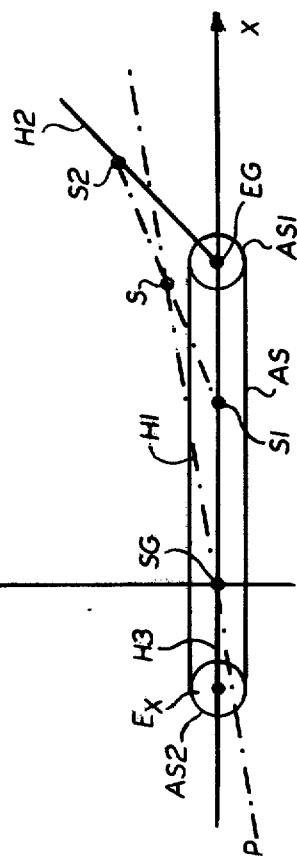
FIG. 1 is a diagram of the basic function of the invention shown in a common plane.

The lever system schematically shown in FIG. 1 consists of individual levers H1 and H2 which form a partial system on the arm side, and a lever H3 on which an eccentric cam Ex is arranged, which together form the partial system on the trunk of the wearer's body. The lever system is mounted to be pivotable about a fulcrum SG. It is to be first of all assumed in the following explanation that the movements of the lever system take place in the plane of the drawing and the arm weight as well as the force P act on the eccentric Ex at right angles to the plane of the drawing.

The individual levers H1 and H2 on the arm run parallel to the upper arm or the lower arm. Points S1 and S2 represent the centers of gravity for the upper arm weight and the lower arm weight, respectively, which the center of gravity of the whole arm is at point S, which rests on the connecting line of the centers S1 and S2. The upper arm and the lower arm are joined together in the elbow joint EG. As will easily be seen from FIG. 1, the change in the center of gravity S in relation to the fulcrum SG, which here lies at the origin of the coordinates x and y, is largely determined by the degree of bending of the forearm. By bending the forearm, the center of gravity moves in direction in relation to the axis passing through the levers H1 and H3 as well as to SG. Taking into account the lever transmission ratio there is produced on bending the forearm, represented by H2 ans S2, first of all a movement about the X axis while at the same time a reduction in the moment about the Y axis. As FIG. 1 shows there are mounted at the elbow articulation point EG and on the lever pulley H3 discs AS1 and AS2 over which a belt AS is laid. The disc AS1 is moved by the rotation of the lever H2 and drives via the belt AS the disc AS2 which forms with the point of application of the force P the eccentric Ex. If the centre of gravity S moves during the pivoting of the individual lever H2 out of the X axis in the direction of positive Y axis, the point of application for the force P shifts in a fixed ratio in the direction of negative Y axis. The X values also vary in opposite direction in relation to the fulcrum SG and there is therefore always equilibrium. It will be seen that through the invention the fulcrum SG and the point of application of the force P and the resultant center of gravity S of the arm lie on a straight line. It must also be mentioned that the above description of the principle in conjunction with FIG. 1 is represented in a single plane.

Figure 2:
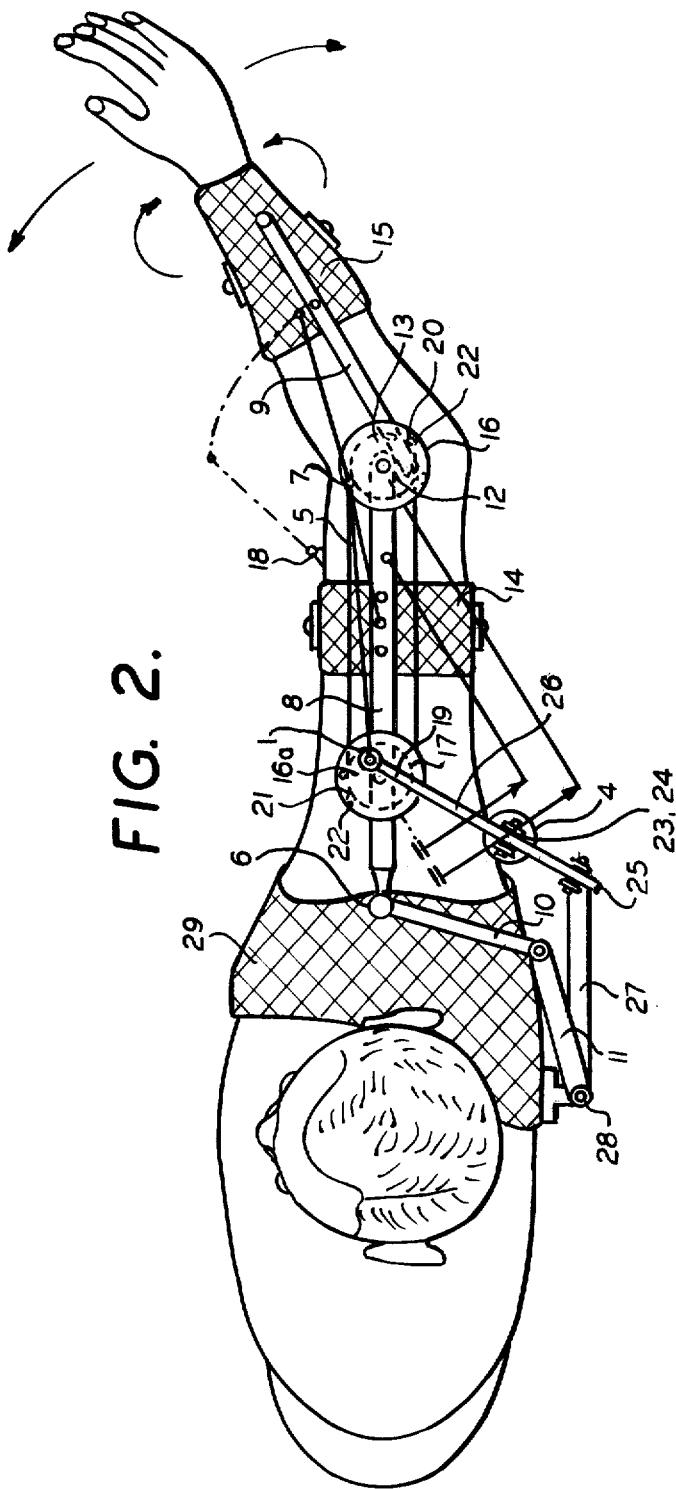
FIG. 2 is a plan view of a first embodiment of the invention.

A first embodiment of the present invention is illustrated in FIG. 1 and 2 which shows the functionally essential parts of the universal orthesis having the operation represented in FIG. 1. In both FIGS. 2 and 3, the same references are used for the same individual parts.

A bodice 29 is fitted on the patient's torso. The bodice 29 consists of a suitable orthopedic material and is matched individually to the patient's body, being attached with belts 30 and 31. A ball joint 6 is mounted on an articulated support 10 which is secured to the bodice 29 by an attachment strip 11.

The ball joint 6 allows spatial movements of the arm relative to the bodice. This ball joint 6 replaces the supporting functions of the natural shoulder joint so that the latter is practically free from load. In conjunction with the upper arm or forearm are individual levers 8 and 9, which consist of extremely light but adequately stable rods. The levers 8 and 9 are secured by means of the bandages 14 and 15 to the upper and lower arms, respectively. On a level with the elbow the rods 8 and 9 are joined by a portable joint 13, which for instance runs in a roller bearing 12. On the joint 13 is mounted a driving pulley disc 16 which rotates with the individual lever 9. On the individual lever 8 is mounted a second pulley disc 16a which is also journalled rotatably in a bearing 17.

On the shoulder pulley disc 16a there is arranged eccentrically a further ball joint 1 to which is connected a curved hoop bracket 26. Between the pulley discs 16 and 16a there is a connection in the form of a belt drive 18. The belt 18 is joined at the points 20 and 21 to the pulley disc 16 and 16a, respectively. The force compensation for the weight of the arm acts via a counterlever 26 on the eccentrically mounted ball joint 1. The ball joint 1 or cardan moves, as already described for FIG. 1, always on the line 5, which moreover passes through the joint 6 and the center of gravity of the arm. The force P acting on the lever 26 is in the form of a closed regenerative double acting or reversible fluid motor having a pair of piston rods 25 and 25a extending from a pressure cylinder 4, to which, for example, compressed air is passed from a supply container 32 via a pressure regulator 2 and a conduit 3. So that this unit can now also perform the necessary movements of the arm, it is attached by means of a multisectionally articulated rod having the parts 25, 27, and 28 via joints 23 and 24 to the bodice 29.

It will readily be seen that the principles illustrated in FIG. 1 providing force equilibrium condition is met, even in the case of movement at right angles to the plane of the drawing.

FIG. 4 shows a side view of another embodiment of the lever system and FIG. 5 a plan thereof. The representation of the unit producing the force and the attachment corset or bodice being dispensed with since it may be the same as shown in FIGS. 2 and 3.

It will be seen from this embodiment that the individual upper arm lever 47 has a hollow profile so that it can be spatially attached to the arm by a movable joint 40 and provide counter lever 50. The hollow section makes it possible for the lever 47 with sufficient inherent stability to accomodate two driving pulley discs 44 and 46 and the driving belt 45. The driving pulley disc 46 has a second or lower arm lever 48 rigidly attached to it and both move in a bearing 42. With the rotation of the lower arm lever 48 and the pulley disc 46 the pulley disc 44 is also rotated. This latter disc 44 is connected with an eccentric pulley disc 43 to which, by means of a spatially movable ball joint or cardan joint 41, the loop or counter bracket 49 is attached.

FIGS. 2 and 3 show a closed fluid preferably a compressed air system for generating the force for holding the equilibrium. The energy supply can, of course, also be any mechanical system, although a pneumatic system or even a hydraulically operated system provides more constructional freedom as regards weight and shape. The orthesis supports all arm movements within the framework of the function of shoulder and elbow joints for those cases in which an arm is weakened by disease, injury, or congenital defficiency in the range from 50 to 85 percent of its normal force or normal functioning capacity.

With the help of this orthesis it is thus possible in spite of the presence of only a small residue of the normal force and/or functioning capacity, to perform many of the normal daily movements and activities such as washing, eating, care of the body, raising small loads, etc.

This means that the orthesis can be used successfully, even if only 15 to 20% of the functional capacity of the arm is retained. The mechanism of the orthesis is designed in such a way that it is able to support the following movements: pushing away, drawing towards, raising the arm forwards and backwards, inward and outward rotation of the arm, circular movement in the shoulder joint, also bending and stretching forwards and backwards in the elbow joint and finally the forward and backward movement of the whole arm. In a word, the arm is able to perform all the movements with the help of the orthesis which are also possible with a sound arm and the arm can also be held in the supported position. Thus even with a small residue of functioning capacity of the arm, lighter activities can still be performed.

The orthesis operates with stored engery, which is controlled by the weakened arm.

This orthesis, which is particularly aimed at the shoulder movements, the upper arm, the elbow joint and the forearm, can be used both by itself and also inconjunction with the known orthesis for the hand. It may also be used in certain cases together with arm prostheses; in this way the functioning possibilities of the prostheses are supported and extended.

A special advantage of the orthesis is to be seen in the fact that its heaviest parts are attached to the chest bodice, while the parts attached to the arm are very light and hardly encumber the weakened arm.

The area of applications for the orthesis is both the therapy of the rehabilitation centers and the treatment in surgical clinics. It should be mentioned that the examples shown here are coordinated with the conditions of equilibrium of the upright human being, but slightly inclined positions are also permitted.

We claim:

1. An orthesis for supporting an arm of a patient whose functional capacity has been diminished comprising an articulated support system adapted to be attached to the trunk and arm of the patient, said support system comprising a fulcrum joint simulating the shoulder joint of the patient and a lever system extending along the arm of the patient, means for applying a force corresponding substantially to the weight of the arm of the patient at a point on said extending lever system substantially lying on a line connecting the fulcrum joint and the center of gravity of the arm of the patient irrespective of the position of the arm of the patient.

2. The orthesis according to claim 1, wherein said lever system includes an upper arm member and a forearm member hinged together at the elbow of the patient and the means for applying said force includes a connecting member adjustable with respect to the upper arm member in response to the movement of said arm.

3. The orthesis according to claim 2, wherein said connecting member comprises a disc rotatably mounted on said upper arm, and said means for applying force thereto includes a link secured to said disc eccentrically of the axis of rotation, and means responsive to the movement of the forearm to rotate said disc thereby varying the point of application of the force.

4. The orthesis according to claim 3, wherein the means responsive to the movement of said forearm comprises a belt connected to said forearm to said disc to rotate the same.

5. The orthesis according to claim 1, wherein said lever system includes a bodice to be worn by the patient, said bodice supporting said fulcrum joint and the means for applying a force.

6. The orthesis according to claim 1, wherein said fulcrum joint is universal joint such as a ball or carden joint.

7. The orthesis according to claim 1, wherein said means for applying said force comprises a reversible motor means mounted on said bodice having a movable link connected to said lever system.

8. The orthesis according to claim 7, wherein said motor means comprises a double acting fluid cylinder and piston, the pistons of which being linked by a pivotal arm to said lever system.

9. The orthesis according to claim 7, wherein said cylinder and piston are connected to a supply of gaseous medium under pressure, mounted on said bodice.

10. The orthesis according to claim 7, wherein a supply of hydraulic fluid under pressure is mounted to said bodice.

11. The orthesis according to claim 7, wherein said pivotal arm is linked to said lever system by a universal joint.

12. The orthesis according to claim 3, wherein said upper and lower arm members are adjustable in length to comform to the length of the patient's arm.

* * * * *